(12) United States Patent
Wrolstad

(10) Patent No.: US 11,963,822 B2
(45) Date of Patent: Apr. 23, 2024

(54) ELECTRICAL GROUNDING FOR IMAGING ASSEMBLY AND ASSOCIATED INTRALUMINAL DEVICES, SYSTEMS, AND METHODS

(71) Applicant: KONINKLIJKE PHILIPS N.V., Eindhoven (NL)

(72) Inventor: David Kenneth Wrolstad, Fallbrook, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 550 days.

(21) Appl. No.: 16/336,544

(22) PCT Filed: Sep. 25, 2017

(86) PCT No.: PCT/EP2017/074156
§ 371 (c)(1),
(2) Date: Mar. 26, 2019

(87) PCT Pub. No.: WO2018/060107
PCT Pub. Date: Apr. 5, 2018

(65) Prior Publication Data
US 2021/0282742 A1    Sep. 16, 2021

Related U.S. Application Data

(60) Provisional application No. 62/401,624, filed on Sep. 29, 2016.

(51) Int. Cl.
*A61B 8/12* (2006.01)
*A61B 8/00* (2006.01)
*A61B 8/08* (2006.01)
*B06B 1/06* (2006.01)

(52) U.S. Cl.
CPC .............. *A61B 8/12* (2013.01); *A61B 8/0891* (2013.01); *A61B 8/445* (2013.01); *B06B 1/0607* (2013.01)

(58) Field of Classification Search
CPC ......... A61B 8/12; A61B 8/445; A61B 8/4444; A61B 8/4455; A61B 8/4483; A61B 8/0891; B06B 1/0292; B06B 1/0633; B06B 1/0607; Y10T 29/49124; Y10T 29/42
See application file for complete search history.

(56) References Cited

U.S. PATENT DOCUMENTS 6,238,347 B1 * 5/2001 Nix .......................... A61B 8/12
600/463
6,618,916 B1 * 9/2003 Eberle .................. A61B 1/0011
264/272.11

(Continued)

*Primary Examiner* — Sean D Mattson
*Assistant Examiner* — Michael Yiming Fang

(57) ABSTRACT

An intraluminal imaging device includes a flexible elongate member sized and shaped for insertion into a vessel of a patient, the flexible elongate member including a proximal portion and a distal portion; an imaging assembly positioned at the distal portion of the flexible elongate member; and a bridge member at electrical ground and in contact with at least a portion of the imaging assembly to maintain the at least portion of the imaging assembly at electrical ground, wherein the bridge member is disposed in cylindrical configuration. Associated devices, systems, and methods are also provided.

22 Claims, 15 Drawing Sheets

(56) References Cited

U.S. PATENT DOCUMENTS

| | | | |
|---|---|---|---|
| 7,226,417 B1* | 6/2007 | Eberle | B06B 1/0633 29/25.35 |
| 7,846,101 B2 | 12/2010 | Eberle et al. | |
| 2014/0187960 A1* | 7/2014 | Corl | B06B 1/0633 29/25.01 |
| 2016/0081657 A1* | 3/2016 | Rice | A61B 8/445 600/301 |
| 2016/0144155 A1* | 5/2016 | Simpson | A61B 5/0066 604/103.05 |
| 2016/0287912 A1* | 10/2016 | Warnking | A61B 8/5207 |
| 2017/0143297 A1* | 5/2017 | Chaggares | H01L 41/00 |
| 2018/0035977 A1* | 2/2018 | Wakabayashi | H04R 17/00 |

\* cited by examiner

ELECTRICAL GROUNDING FOR IMAGING ASSEMBLY AND ASSOCIATED INTRALUMINAL DEVICES, SYSTEMS, AND METHODS

This application is the U.S. National Phase application under 35 U.S.C. § 371 of International Application No. PCT/EP2017/074156, filed on Sep. 25, 2017, which claims the benefit of Provisional Application Ser. No. 62/401,624, filed Sep. 29, 2016. These applications are hereby incorporated by reference herein.

TECHNICAL FIELD

The present disclosure relates generally to intraluminal imaging and, in particular, to an imaging assembly of an intraluminal imaging device. For example, the imaging assembly can include bridge member that provides electrical grounding for one or more components of a flex circuit.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Electrical signals are transmitted to the various components of the imaging assembly during using of the imaging assembly. Operating imaging assembly properly may require maintaining one or more components at electrical ground. Some extant devices rely on a metallic support member that is part of the imaging assembly. The metallic support member however limits the ability to manufacture a more flexible device that can more easily traverse tortuous vasculature.

SUMMARY

The invention provides imaging devices, systems, and related methods that overcome the limitations of imaging assemblies having one or more components that need electrical grounding.

Embodiments of the present disclosure provide an improved intraluminal imaging system for generating images of a blood vessel. An imaging assembly includes metallic bridge member that is maintained at electrical ground. The bridge member is disposed within the imaging assembly such that the bridge member contacts the one or more components that need to be held at electrical ground. For example, the bridge member may contact one or more imaging elements. Advantageously, by providing a bridge member for electrical ground, other components of the imaging assembly can be simplified. For example, a more flexible and a more cost efficient support member, with a less complex geometry, may be implemented in the imaging assembly.

In one embodiment, an intraluminal imaging device is provided. The intraluminal imaging device includes a flexible elongate member configured for insertion into a vessel of a patient, the flexible elongate member including a proximal portion and a distal portion; an imaging assembly positioned at the distal portion of the flexible elongate member; and a bridge member at electrical ground and in contact with at least a portion of the imaging assembly to maintain the at least portion of the imaging assembly at electrical ground, wherein the bridge member is disposed in cylindrical configuration.

In some embodiments, the imaging assembly includes a flex circuit and a support member, wherein the bridge member is in contact with at least a portion of the flex circuit. In some embodiments, the support member comprises a non-conductive material and the bridge member comprises a conductive material. In some embodiments, the bridge member is wrapped around the support member. In some embodiments, the flex circuit is wrapped around the bridge member. In some embodiments, the flex circuit comprises a plurality of controllers in communication with a plurality of imaging elements, wherein the bridge member is in contact with the plurality of imaging elements. In some embodiments, proximal region and distal region of the flex circuit and the bridge member are coupled. In some embodiments, the bridge member includes a proximal portion, a distal portion, and a plurality of ribs extending between the proximal portion and the distal portion. In some embodiments, the plurality of ribs are in contact with the at least a portion of the imaging assembly. In some embodiments, the bridge member includes a proximal region, a distal region, and a central region, wherein the proximal and distal regions include a larger diameter than the central region. In some embodiments, the bridge member comprises a first transition region between the proximal region and the central region and a second transition region between the distal region and the central region, wherein the first and second transition regions include a larger diameter than the central region and a smaller diameter than the proximal and distal regions. In some embodiments, the bridge member is configured to be transitioned from a flat configuration into a cylindrical configuration. In some embodiments, the bridge member is coupled to an electrical wire extending along a length of the flexible elongate member.

In one embodiment, a method of assembling an intraluminal imaging device is provided. The method includes obtaining an imaging assembly comprising a flex circuit in a flat configuration; obtaining a bridge member in a flat configuration; coupling the bridge member to the flex circuit while the flex circuit and the bridge member are in the flat configuration; and transitioning the flex circuit and the bridge member into a cylindrical configuration.

In some embodiments, the imaging assembly includes a support member made of a non-conductive material, and wherein the transitioning includes wrapping the bridge member around the support member. In some embodiments, the transitioning includes wrapping the flex circuit around the bridge member. In some embodiments, the coupling includes applying adhesive to proximal and distal regions of at least one of the flex circuit or the bridge member. In some embodiments, the flex circuit comprises a plurality of controllers in communication with a plurality of imaging elements, and wherein the coupling includes contacting the bridge member to the plurality of imaging elements. In some embodiments, the bridge member comprises a proximal region, a distal region, and a plurality of ribs extending between the proximal region and the distal region, and wherein the contacting includes contacting the plurality of ribs to the plurality of imaging elements. In some embodiments, the method includes coupling an electrical wire at electrical ground to the bridge member.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
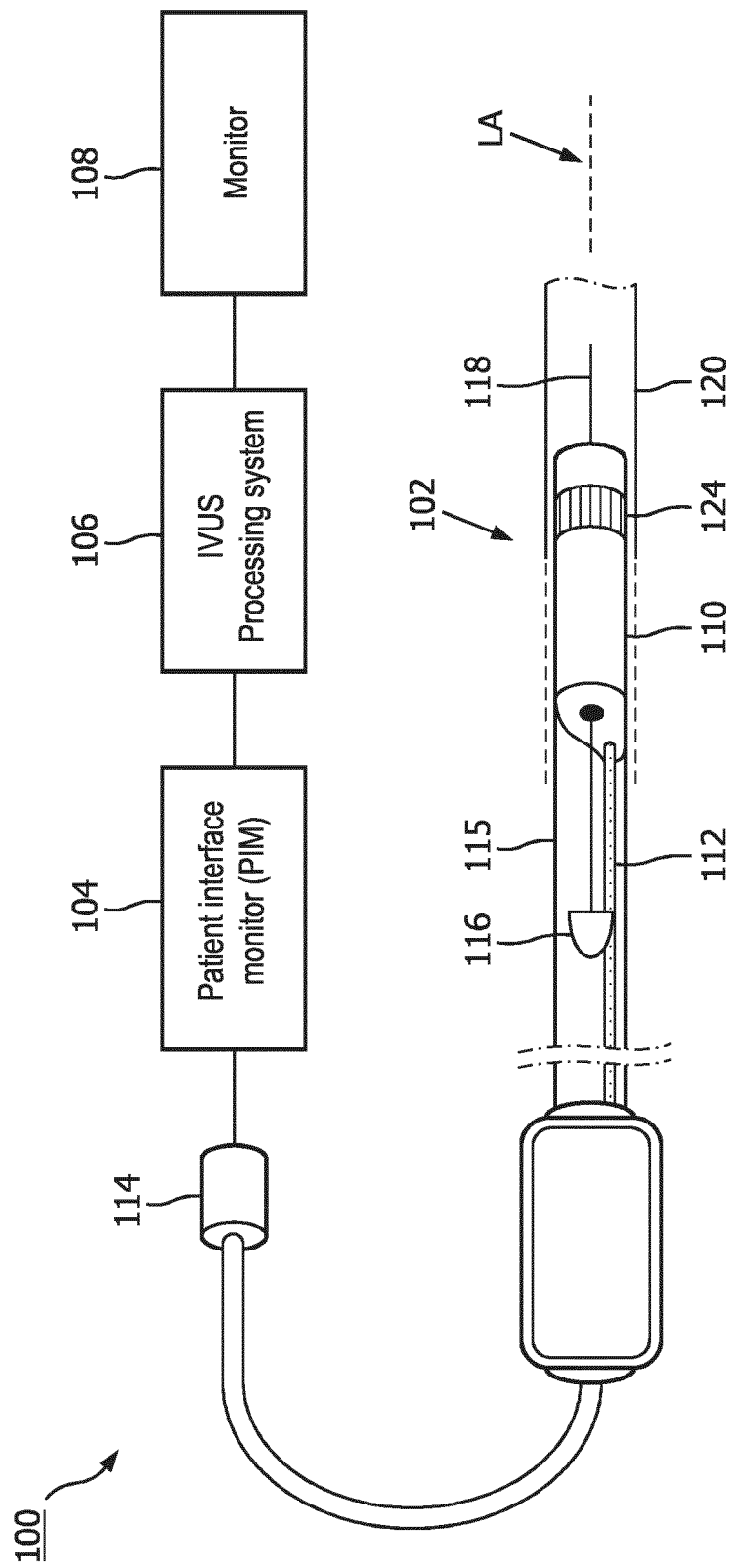
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure describes an imaging assembly for an intraluminal imaging device. The imaging assembly includes a flex circuit positioned at a distal portion of a flexible elongate member. One or more components of the flex circuit are in contact with a bridge member. For example, the imaging elements and/or the controllers can contact the bridge member. The bridge member maintains the components it is in contact with at electrical ground. The bridge member, like the flex circuit, can be transitioned from a flat configuration to a rolled/cylindrical configuration.

The intraluminal imaging device described herein achieves numerous advantages. For example, providing a bridge member to provide electrical ground alleviates the responsibility for the support member to provide electrical grounding. Whereas extant devices relied upon a metallic support member with a relatively complex geometry, the present invention allows for non-metallic support members with relatively less complex geometry. A non-metallic support member may also be more flexible, which contributes to the overall improvement in flexibility for the imaging assembly to maneuver through tortuous vessel easily. The current invention may also allow for a more cost-efficient guide member. Assembling the bridge member with the flex circuit does not reduce manufacturing efficiency because the bridge member can be incorporated into the processes for forming the flex circuit.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
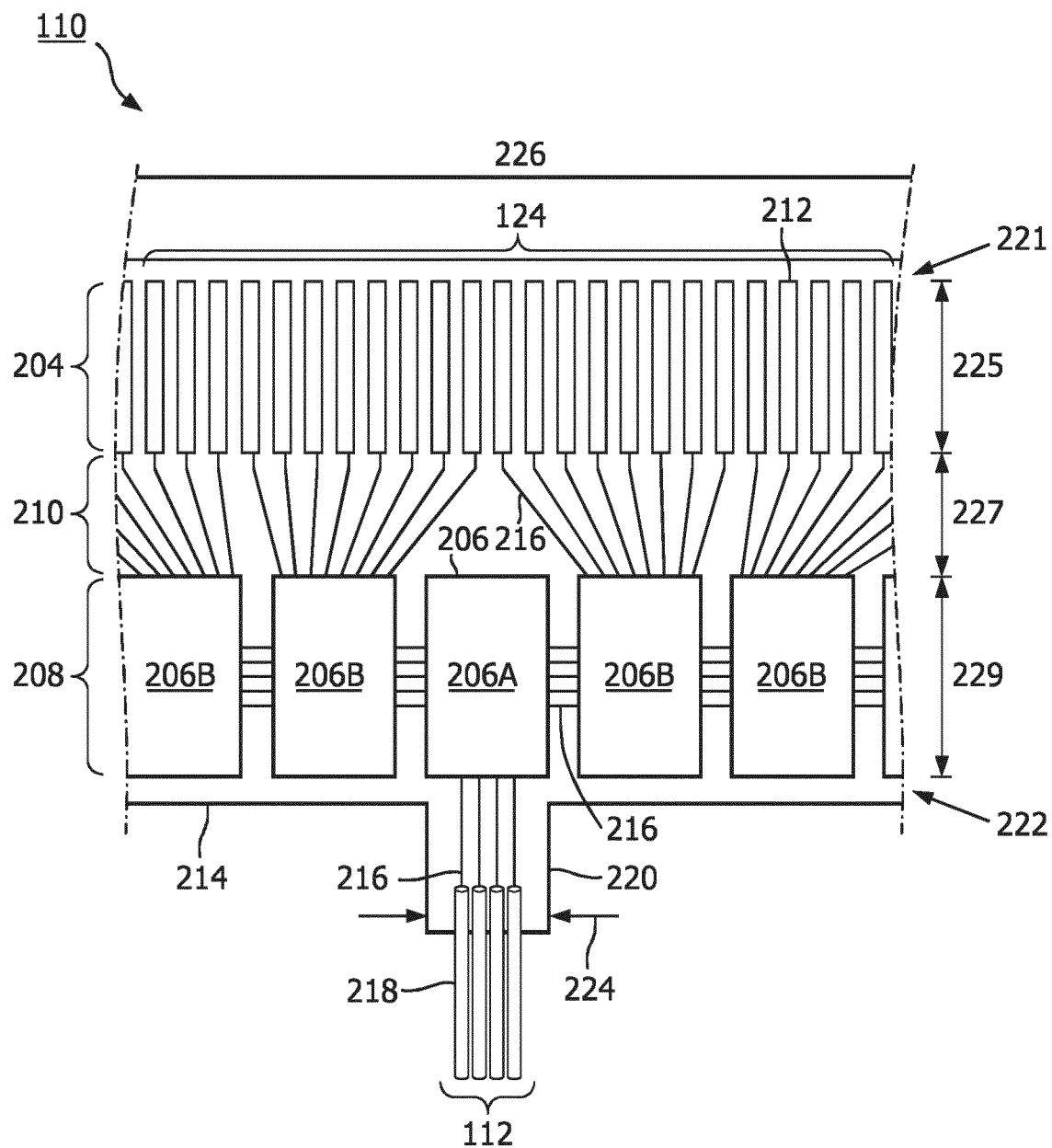
FIG. 2 is a diagrammatic top view of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

The IVUS device 102 includes a flexible elongate member 115 having a proximal portion and a distal portion. The scanner assembly 110 is positioned at a distal portion of the flexible elongate member 115. The flexible elongate member 115 includes a longitudinal axis LA. The longitudinal axis LA may be associated with the IVUS device 102 and/or the imaging assembly 110.

Figure 3:
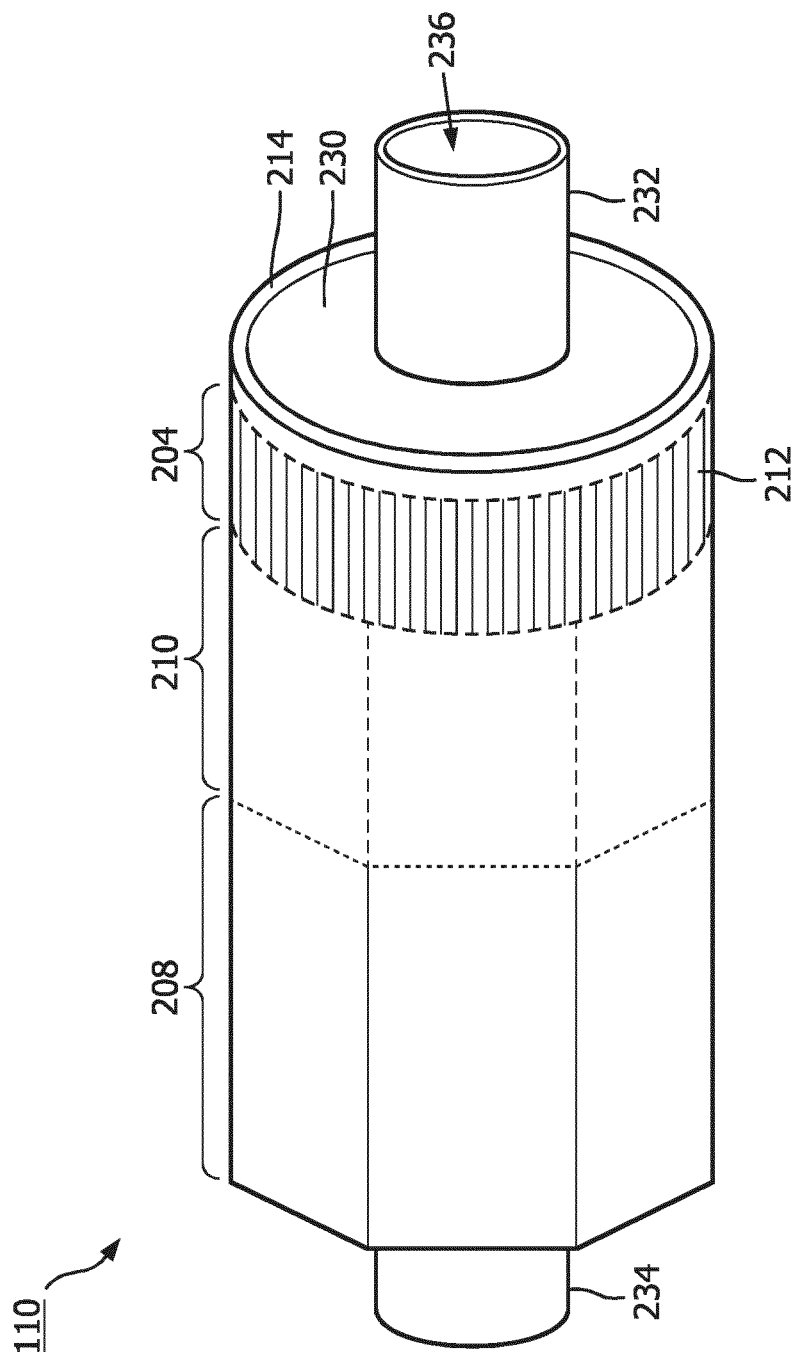
FIG. 3 is a diagrammatic side view of a scanner assembly in a rolled configuration around a support member, according to aspects of the present disclosure.

FIG. 2 is a top view of a portion of an ultrasound scanner assembly 110 according to an embodiment of the present disclosure. The assembly 110 includes a transducer array 124 formed in a transducer region 204 and transducer control logic dies 206 (including dies 206A and 206B) formed in a control region 208, with a transition region 210 disposed therebetween. The transducer control logic dies 206 and the transducers 212 are mounted on a flex circuit 214 that is shown in a flat configuration in FIG. 2. FIG. 3 illustrates a rolled configuration of the flex circuit 214. The transducer array 202 is a non-limiting example of a medical sensor element and/or a medical sensor element array. The transducer control logic dies 206 is a non-limiting example of a control circuit. The transducer region 204 is disposed adjacent a distal portion 221 of the flex circuit 214. The control region 208 is disposed adjacent the proximal portion 222 of the flex circuit 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or a length 227 of the transition region 210 can be greater than lengths 225, 229 of the transducer region and controller region, respectively. While the imaging assembly 110 is described as including a flex circuit, it is understood that the transducers and/or controllers may be arranged to form the imaging assembly 110 in other configurations, including those omitting a flex circuit.

The transducer array 124 may include any number and type of ultrasound transducers 212, although for clarity only a limited number of ultrasound transducers are illustrated in FIG. 2. In an embodiment, the transducer array 124 includes 64 individual ultrasound transducers 212. In a further embodiment, the transducer array 124 includes 32 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, capacitive micromachined ultrasound transducers (cMUTs), single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

The flex circuit 214, on which the transducer control logic dies 206 and the transducers 212 are mounted, provides structural support and interconnects for electrical coupling. The flex circuit 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIG. 2, the flex circuit 214 has a generally rectangular shape. As shown and described herein, the flex circuit 214 is configured to be wrapped around a support member 230 (FIG. 3) to form a cylindrical toroid in some instances. Therefore, the thickness of the film layer of the flex circuit 214 is generally related to the degree of curvature in the final assembled scanner assembly 110. In some embodiments, the film layer is between 5 µm and 100 µm, with some particular embodiments being between 12.7 µm and 25.1 µm.

To electrically interconnect the control logic dies 206 and the transducers 212, in an embodiment, the flex circuit 214 further includes conductive traces 216 formed on the film layer that carry signals between the control logic dies 206 and the transducers 212. In particular, the conductive traces 216 providing communication between the control logic dies 206 and the transducers 212 extend along the flex circuit 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214. Suitable materials for the conductive traces 216 include copper, gold, aluminum, silver, tantalum, nickel, and tin, and may be deposited on the flex circuit 214 by processes such as sputtering, plating, and etching. In an embodiment, the flex circuit 214 includes a chromium adhesion layer. The width and thickness of the conductive traces 216 are selected to provide proper conductivity and resilience when the flex circuit 214 is rolled. In that regard, an exemplary range for the thickness of a conductive trace 216 and/or conductive pad is between 10-50 µm. For example, in an embodiment, 20 µm conductive traces 216 are separated by 20 µm of space. The width of a conductive trace 216 on the flex circuit 214 may be further determined by the width of the conductor 218 to be coupled to the trace/pad.

The flex circuit 214 can include a conductor interface 220 in some embodiments. The conductor interface 220 can be a location of the flex circuit 214 where the conductors 218 of the cable 112 are coupled to the flex circuit 214. For example, the bare conductors of the cable 112 are electrically coupled to the flex circuit 214 at the conductor interface 220. The conductor interface 220 can be tab extending from the main body of flex circuit 214. In that regard, the main body of the flex circuit 214 can refer collectively to the transducer region 204, controller region 208, and the transition region 210. In the illustrated embodiment, the conductor interface 220 extends from the proximal portion 222 of the flex circuit 214. In other embodiments, the conductor interface 220 is positioned at other parts of the flex circuit 214, such as the distal portion 221, or the flex circuit 214 omits the conductor interface 220. A value of a dimension of the tab or conductor interface 220, such as a width 224, can be less than the value of a dimension of the main body of the flex circuit 214, such as a width 226. In some embodiments, the substrate forming the conductor interface 220 is made of the same material(s) and/or is similarly flexible as the flex circuit 214. In other embodiments, the conductor interface 220 is made of different materials and/or is comparatively more rigid than the flex circuit 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flex circuit 214, the conductor interface 220 and/or the conductor(s) 218 can be variously configured to facilitate efficient manufacturing and operation of the scanner assembly 110.

Figure 4:
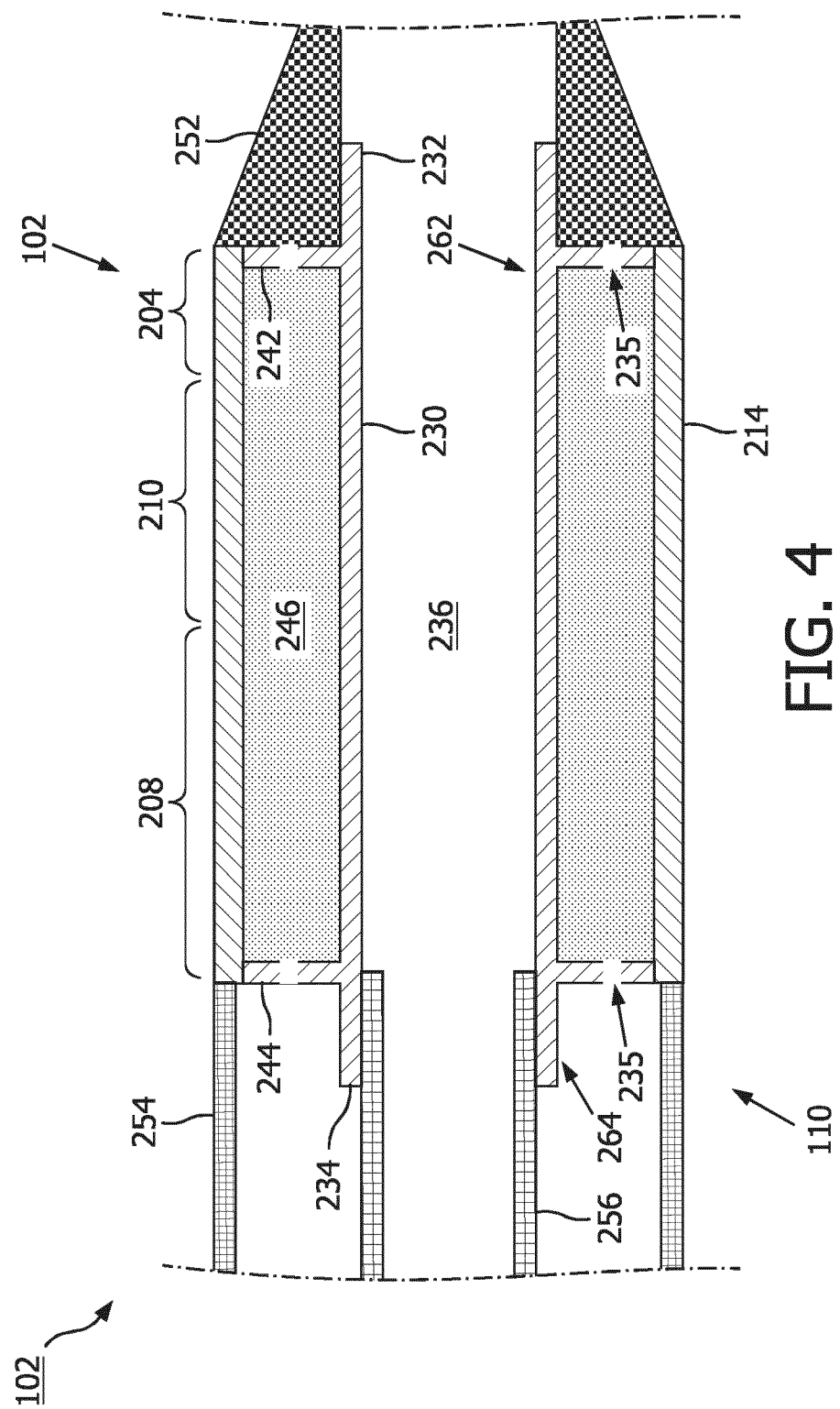
FIG. 4 is a diagrammatic cross-sectional side view of a distal portion of an intraluminal device, according to aspects of the present disclosure.

In some instances, the scanner assembly 110 is transitioned from a flat configuration (FIG. 2) to a rolled or more cylindrical configuration (FIGS. 3 and 4). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

As shown in FIGS. 3 and 4, the flex circuit 214 is positioned around the support member 230 in the rolled configuration. FIG. 3 is a diagrammatic side view with the flex circuit 214 in the rolled configuration around the support member 230, according to aspects of the present disclosure. FIG. 4 is a diagrammatic cross-sectional side view of a distal portion of the intraluminal device 102, including the flex circuit 214 and the support member 230, according to aspects of the present disclosure.

The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The support member 230 can be ferrule having a distal portion 262 and a proximal portion 264. The support member 230 can define a lumen 236 extending longitudinally therethrough. The lumen 236 is in communication with the exit port 116 and is sized and shaped to receive the guide wire 118 (FIG. 1). The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule and stands 242, 244, that are fixedly coupled to one another.

Stands 242, 244 that extend vertically are provided at the distal and proximal portions 262, 264, respectively, of the support member 230. The stands 242, 244 elevate and support the distal and proximal portions of the flex circuit 214. In that regard, portions of the flex circuit 214, such as the transducer portion 204, can be spaced from a central body portion of the support member 230 extending between the stands 242, 244. The stands 242, 244 can have the same outer diameter or different outer diameters. For example, the distal stand 242 can have a larger or smaller outer diameter than the proximal stand 244. To improve acoustic performance, any cavities between the flex circuit 214 and the surface of the support member 230 are filled with a backing material 246. The liquid backing material 246 can be introduced between the flex circuit 214 and the support member 230 via passageways 235 in the stands 242, 244. In some embodiments, suction can be applied via the passageways 235 of one of the stands 242, 244, while the liquid backing material 246 is fed between the flex circuit 214 and the support member 230 via the passageways 235 of the other of the stands 242, 244. The backing material can be cured to allow it to solidify and set. In various embodiments, the support member 230 includes more than two stands 242, 244, only one of the stands 242, 244, or neither of the stands. In that regard the support member 230 can have an increased diameter distal portion 262 and/or increased diameter proximal portion 264 that is sized and shaped to elevate and support the distal and/or proximal portions of the flex circuit 214.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can be flexible elongate member that extend from proximal portion of the intraluminal device 102, such as the proximal connector 114, to the imaging assembly 110. For example, the proximal inner member 256 can be received within a proximal flange 234. The proximal outer member 254 abuts and is in contact with the flex circuit 214. A distal member 252 is coupled to the distal portion 262 of the support member 230. The distal member 252 can be a flexible component that defines a distal most portion of the intraluminal device 102. For example, the distal member 252 is positioned around the distal flange 232. The distal member 252 can abut and be in contact with the flex circuit 214 and the stand 242. The distal member 252 can be the distal-most component of the intraluminal device 102.

One or more adhesives can be disposed between various components at the distal portion of the intraluminal device 102. For example, one or more of the flex circuit 214, the support member 230, the distal member 252, the proximal inner member 256, and/or the proximal outer member 254 can be mechanically coupled to one another via an adhesive.

Figure 5:
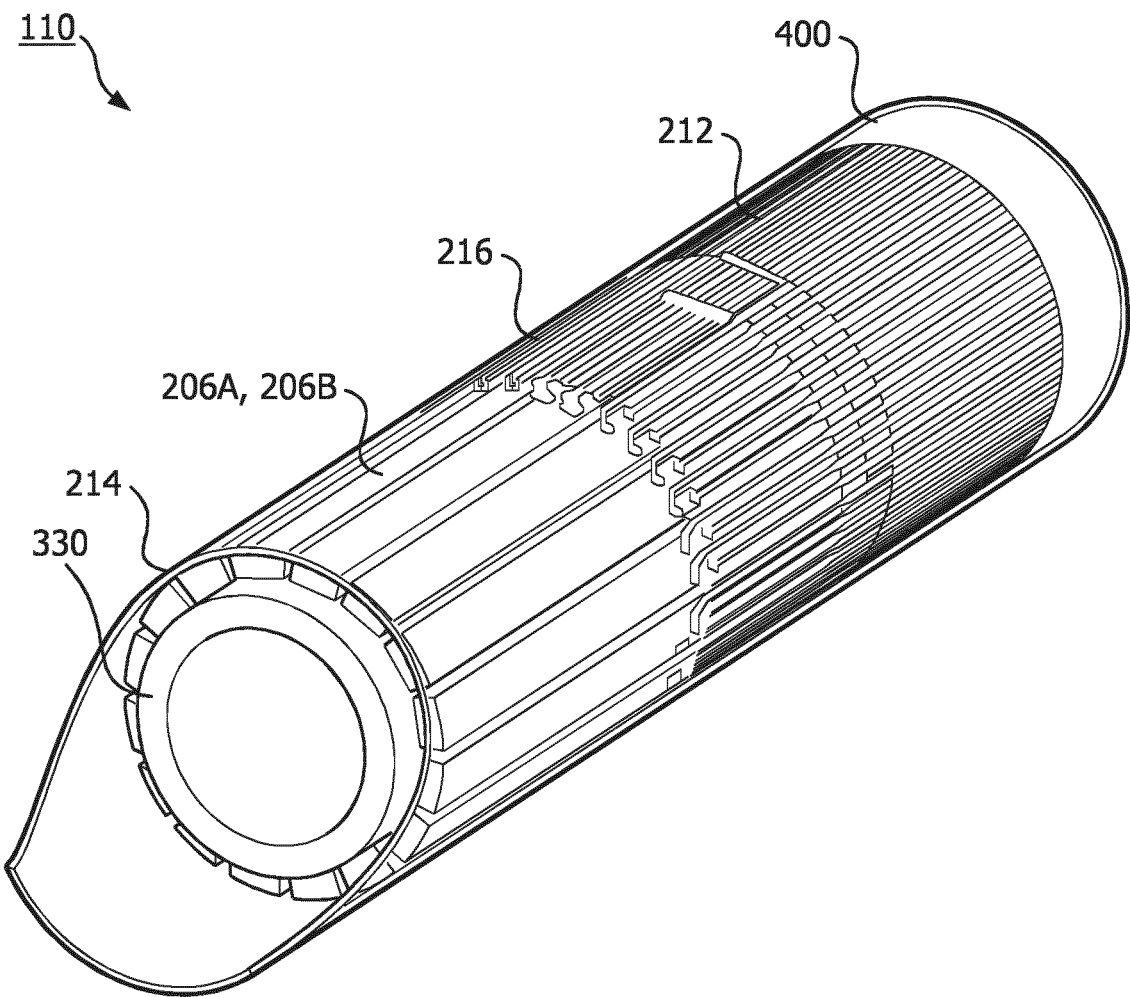
FIG. 5 is a diagrammatic perspective view of an imaging assembly including a bridge member, according to aspects of the present disclosure.

FIG. 5 is a diagrammatic perspective view of an exemplary embodiment of the imaging assembly 110. The imaging assembly includes a flex circuit 214, a support member 330, and a bridge member 400. The bridge member 400 is in contact with one or more components of the flex circuit 214, such as the controllers 206A, 206B and/or the transducer elements 212. In an exemplary embodiment, the bridge member 400 is in contact with the transducer elements 212. The bridge member 400 is at electrical ground. As a result of the contact, the bridge member 400 maintains the one or more components of the flex circuit 214 at electrical ground during operation of the imaging assembly 110. In FIG. 5, the flex circuit 214 and the bridge member 400 are shown to be in a rolled or cylindrical configuration. For example, the bridge member 400 can be wrapped in a cylindrical configuration around the support member 330. The flex circuit 314 can be wrapped in a cylindrical configuration around the bridge member 400.

Figure 6:
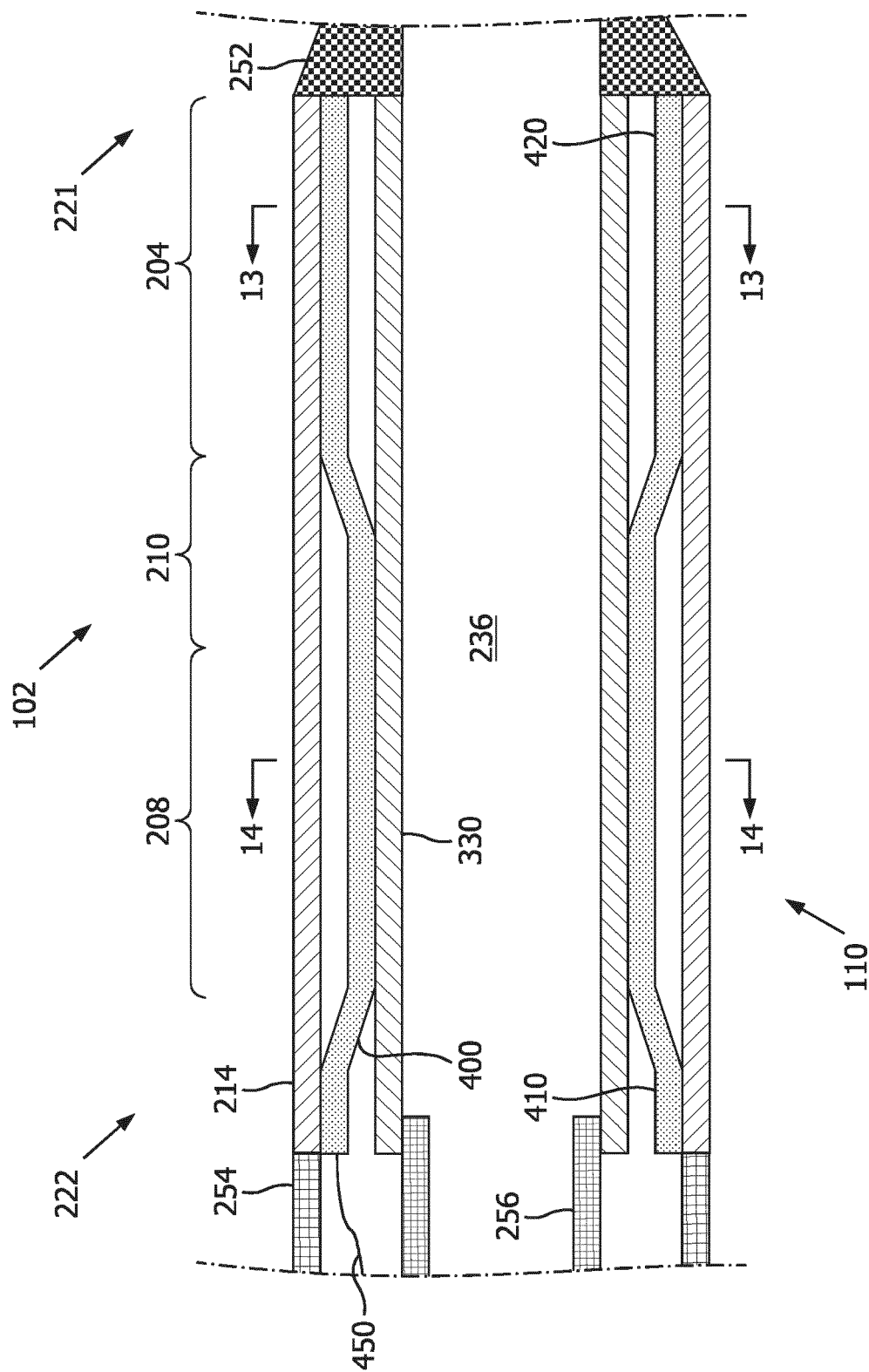
FIG. 6 is a diagrammatic cross-sectional side view of an imaging assembly including a bridge member, according to aspects of the present disclosure.

FIG. 6 is a diagrammatic cross-sectional side view of a distal portion of the intraluminal device 102, including the imaging assembly 110. The bridge member 400, as well as the flex circuit 214 and the support member 330, extend longitudinally in a substantially parallel manner as the longitudinal axis LA. The bridge member 400 can be positioned between the flex circuit 214 and support member.

At least a portion of the flex circuit 214 is in electrical communication with the bridge member 400. In that regard, the bridge member 400 is in contact with the transducer region 204 of the flex circuit 214. The bridge member 400 is spaced from the controller region 208 of the flex circuit 214. As a result of contact between the bridge member 400 and the transducer region 204, the transducer elements 212 are maintained at electrical ground while positive and/or negative voltages are transmitted to the controllers 206A, 206B in the controller region 208. Electrical signals can be transmitted to the controllers 206A, 206B by wires of the electrical cable 112 (FIG. 2). As shown in FIG. 6, the bridge member 400 can be in communication with an electrical wire 450. The electrical wire 450 is maintained at electrical ground. Accordingly, the bridge member 400 and the transducer elements 212 of the transducer region 204 are also at electrical ground. The electrical wire 450 can be one of the conductors 218 of the electrical cable 112 (FIG. 2) in some embodiments.

The flex circuit 214 is mechanically coupled to the bridge member 400. For example, adhesive may be positioned on the flex circuit 214 and/or the bridge member 400 to affix the components together. For example, the proximal portion 222 of the flex circuit 214 can be bonded to the proximal region 410 of the bridge member 400. The distal portion 221 of the flex circuit 214 can be bonded to the distal region 420 of the bridge member 400. In some embodiments, other portions of the bridge member 400 can be bonded to other portions of the flex circuit 214.

The bridge member 400 is formed of a conductive material, such as a metal or metal alloy, including copper, gold, aluminum, silver, tantalum, nickel, tin, combinations thereof, and/or other suitable materials. In some embodiments, the bridge member 400 is formed of a single material. In some embodiments, the bridge member 400 can be plated. For example, the bridge member 400 can be formed of a first material that is coated with a second material with better conductive properties than the first material. For example, the bridge member 400 can be formed of nickel or copper, with gold plating.

The features of the support member 330 can be similar to those of the support member 230 (FIG. 4). In some instances, the structure of the support member 330 can be substantially similar to that of the support member 230. In the illustrated embodiment of FIG. 6, the support member 300 is a tubular or cylindrical component around which the bridge member 400 is wrapped. The support member 330 may be formed of a non-conductive material, such as plastic, thermoplastic, polymer, hard polymer, etc. For example, the support member 330 can be made of polyimide, polyester, polyethylene napthalate, polyetherimide, polyether ether ketone (PEEK), and/or other suitable materials. In some embodiments, the acoustic backing material 246 is positioned adjacent to the flex circuit 214, such as between the transducer region 204 and the support member 330 and/or between the transducer region 204 and the bridge member 400.

The embodiment of FIG. 6 also includes features similar to those described with respect to FIG. 4, includes the outer member 254, the inner member 256, the lumen 236 of the support member, and the distal member 252. One or more of the conductors 218 of the electrical cable 112 can extend along the length of the flexible elongate member 115 within the outer member 254, and/or between the outer member 254 and the inner member 256.

Figure 7:
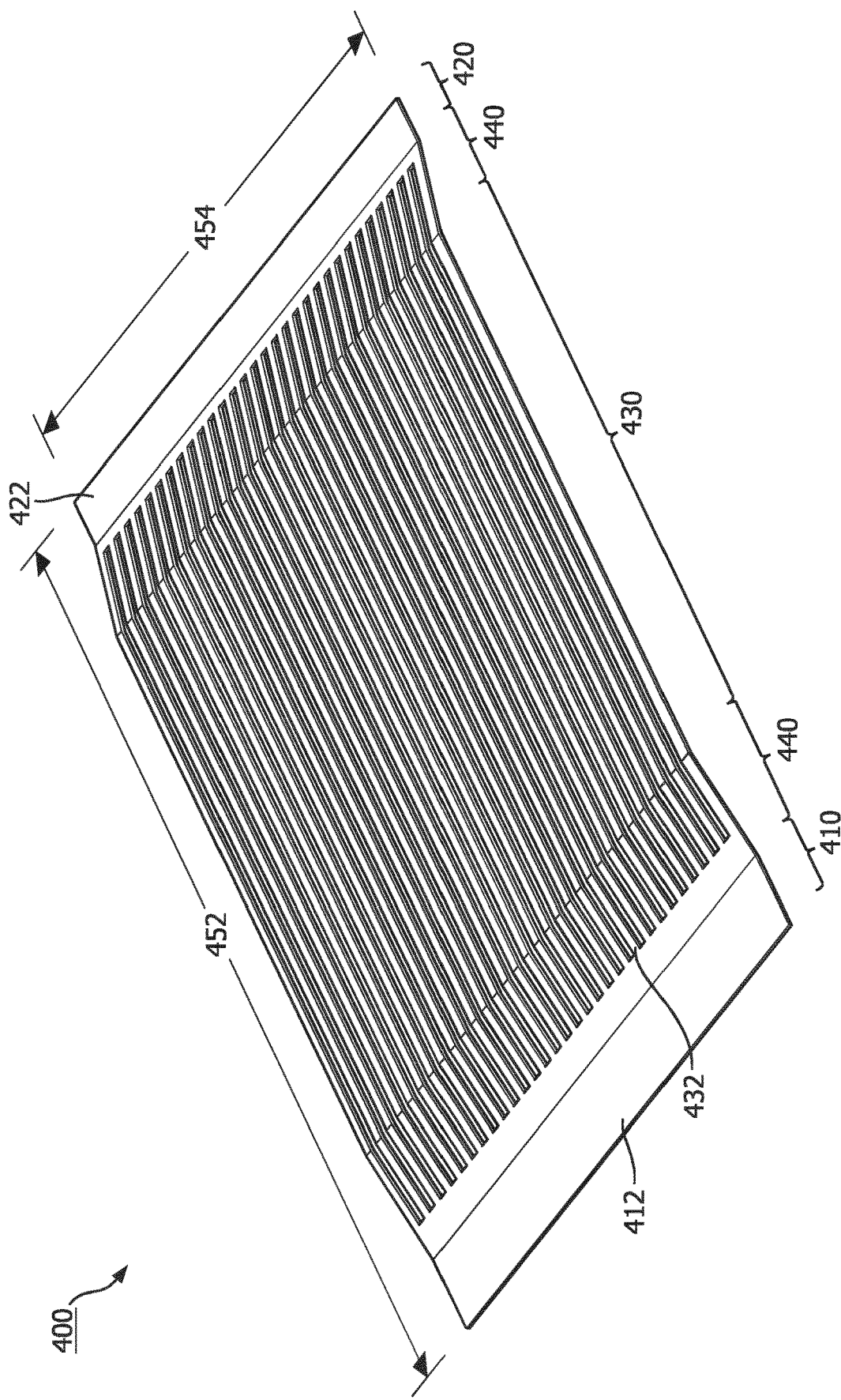
FIG. 7 is a diagrammatic perspective view of a bridge member in a flat configuration, according to aspects of the present disclosure.
Figure 8:
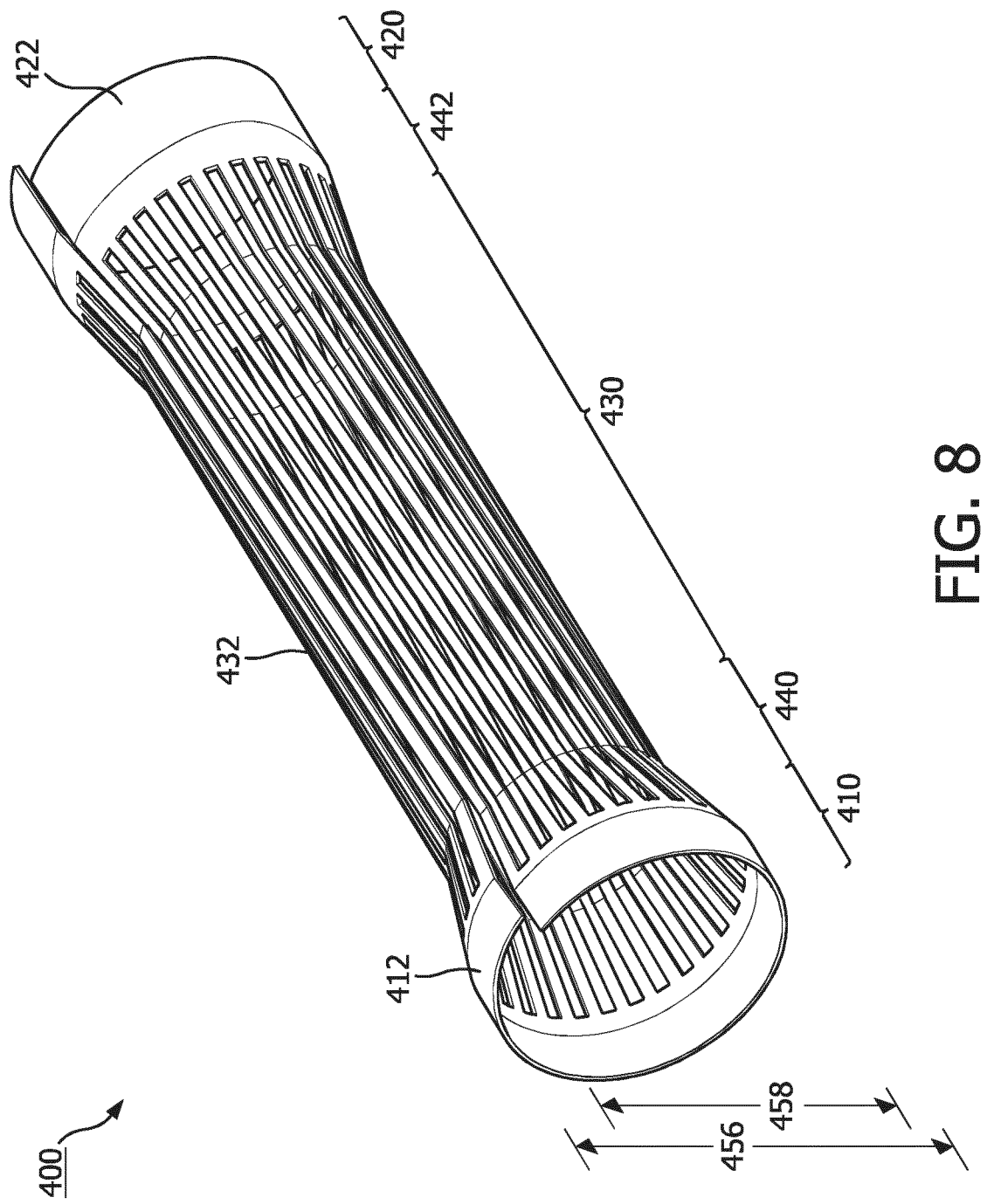
FIG. 8 is a diagrammatic perspective view of a bridge member in a rolled configuration, according to aspects of the present disclosure.

FIGS. 7 and 8 are diagrammatic perspective views of the bridge member 400. FIG. 7 illustrates the bridge member 400 in a flat configuration, and FIG. 8 illustrates the bridge member 400 in a rolled or cylindrical configuration. Generally, the bridge member 400 sized, shaped, and/or otherwise structured to facilitate contact with one or more components of the flex circuit 214. For example, the bridge member 400 can be arranged to contact the transducer elements 212 to maintain the transducers 212 at electrical ground. In some embodiments, the bridge member 400 can be arranged to contact the controllers 206A, 206B to maintain the controllers 206A, 206B at electrical ground. In some embodiments, a portion of the bridge member 400 can be arranged to contact the transducer elements 212 and another portion of the bridge member 400 is arranged to contact the controllers 206A, 206B. The bridge member 400 can be formed by any suitable process, including micromachining, 3D printing, wafer production processes, etc.

In a flat configuration of FIG. 7, the bridge member 400 has a length 452 in a direction parallel to the longitudinal axis LA and a width 454 perpendicular to the longitudinal axis LA. The length 452 may be any suitable value, including between approximately 0.05" and 0.5", for example. The width 454 may be any suitable value, including between approximately 0.075" and 0.5", for example. In some embodiments, the dimensions of the bridge member 400, such as the length 452 and/or the width 454 may be selected based on one or more dimensions of components of the intraluminal device 102 that mate, adjoin, contact, and/or otherwise couple with the imaging assembly 110. For example, the dimensions of the bridge member 400 can be selected on the dimensions of the flex circuit 214, the support member 330, the inner member 256, the outer member 254, the distal member 252, and/or other components. In some embodiments, the width 454 can be selected based on the size of the intraluminal device 102, which can be between approximately 2 Fr and 12 Fr, for example. In some embodiments, the length 452 and the width 454 may be substantially equal to the length and width of the flex circuit 214.

The bridge member 400 includes the proximal region 410 and the distal region 420. A planar component 412 is provided at the proximal region 410, and a planar component 422 is provided at the distal region 420. Respective surfaces of the planar components 412, 422 adjacent to the flex circuit 214 are bonded to the flex circuit 214 to couple the bridge member 400 and the flex circuit 214. In some embodiments, the surface areas of the planar components 412, 422 are substantially equal. In some embodiments, the surface area of the planar component 412 or the planar component 422 can be larger than the other. In the illustrated embodiment, for example, the planar component 412 is larger than the planar component 422. The length and/or width of one of the planar components 412, 422 may be larger than the other.

A central region 430 of the bridge member 400 is disposed between proximal and distal regions 410, 420. In the rolled or cylindrical configuration, the diameter of the bridge member 400 can vary between the proximal region 410 and the distal region 420. For example, as shown in FIG. 8, the central region 430 can have a diameter 458 that is smaller than the diameter 456 of the proximal and distal regions 410, 420. The diameter 456 of the proximal and distal regions 410, 420 can be any suitable value, including between approximately 0.025" and 0.160", for example. The diameter 458 of the central region 430 can be any suitable value, including between approximately 0.0125" and 0.150", for example. In some embodiments, the diameter 456 and diameter 458 can be selected based on the size of the intraluminal device 102 and/or one or more components of the intraluminal device. For example, the diameter 456 and/or the diameter 458 can be based on the width 454. The bridge member 400 also includes transition regions 440, 442. The transition regions 440, 442 have changing diameters. The diameters of the transition regions 440, 442 taper or decrease from the larger diameter 456 of the proximal and distal regions 410, 420, respectively, to the smaller diameter 458 of the central region 430. The diameters of the transition regions 440, 442 increase from the smaller diameter 458 of the central region 430 to the larger diameter 456 of the proximal and distal regions 410, 420, respectively.

A plurality of ribs 432 extends longitudinally between the proximal region 410 and the distal region 420. The bridge member 400 includes any suitable number of ribs. In some instances, the number of ribs 432 is related to the number of transducer elements 212. For example, the bridge member 400 may the same number of ribs 432 as there are transducer elements 212. For example, when there can be sixty four ribs 432 when there are sixty four transducer elements 212. In such embodiments, each transducer element 212 is in contact with one respective rib 432. In other instances, a single rib 432 may be in contact with two or more transducer elements 212. For example, the total number of ribs 432 may be half of the total number of transducer elements 212. The ribs may be spaced apart from one another by any suitable distance, including between approximately 0.001" and 0.020", for example.

Figure 11:
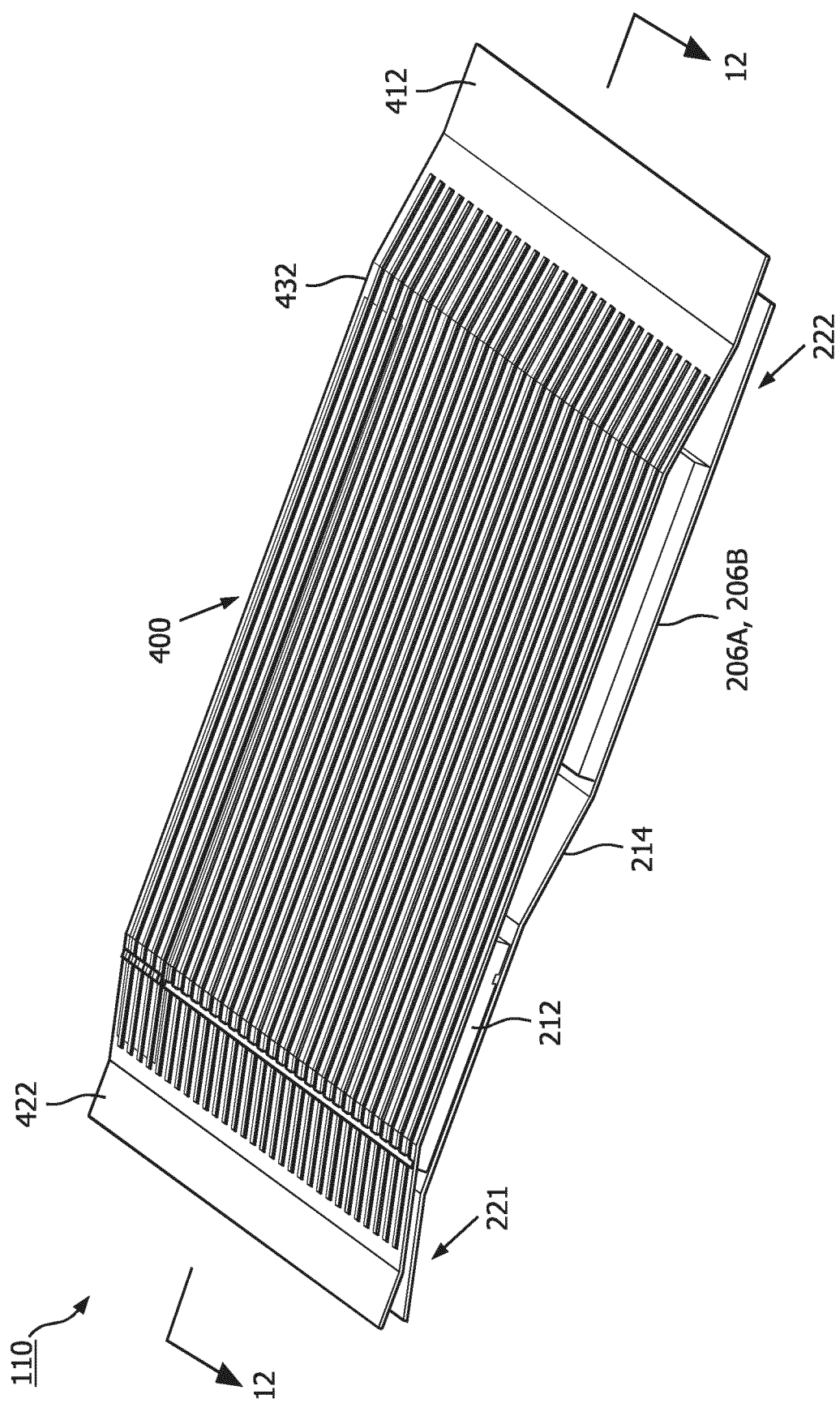
FIG. 11 is diagrammatic perspective view of a support member and a flex circuit in a flat configuration.
Figure 12:
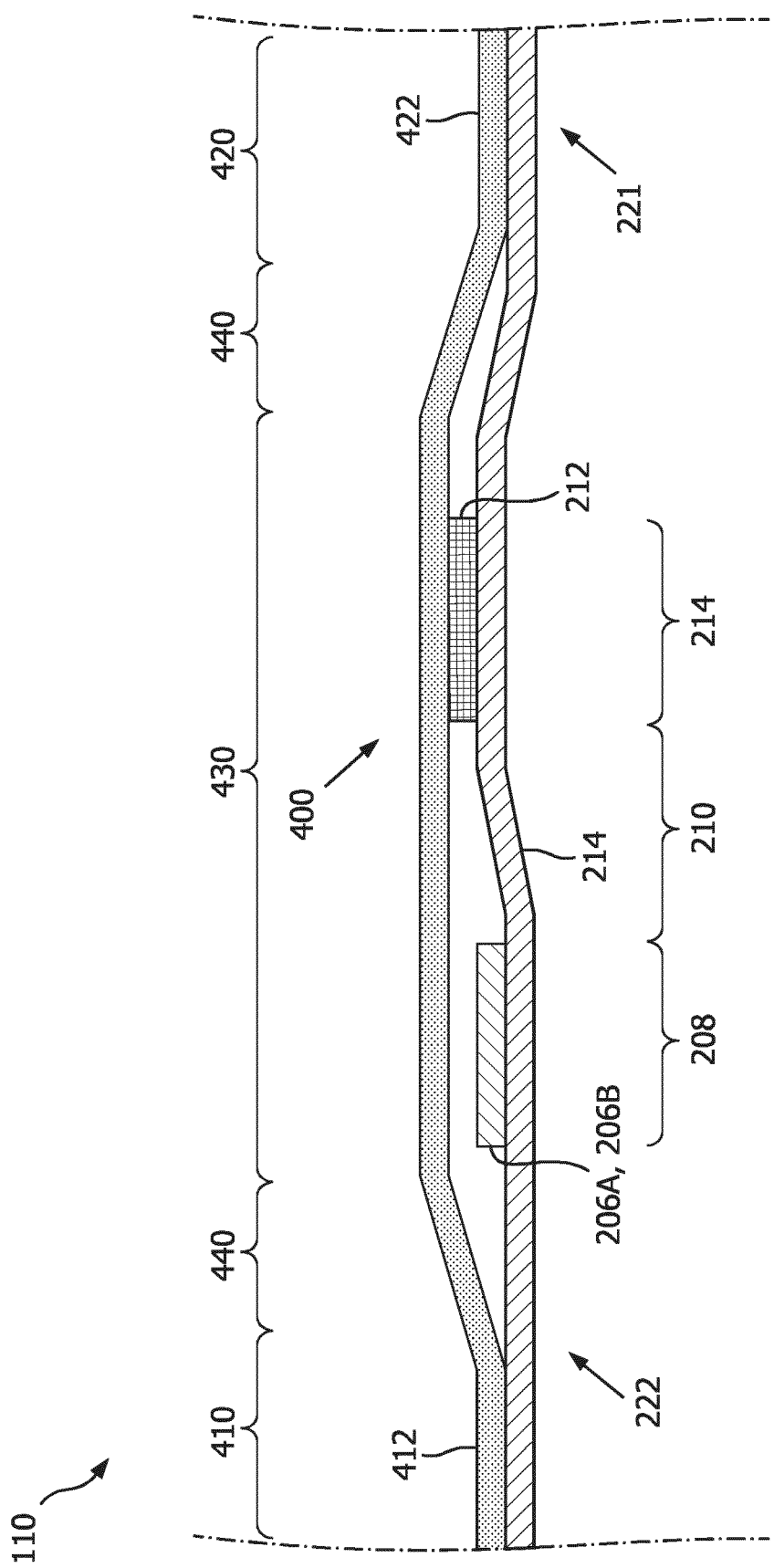
FIG. 12 is diagrammatic cross-section side view of a support member and a flex circuit in a flat configuration.
Figure 13:
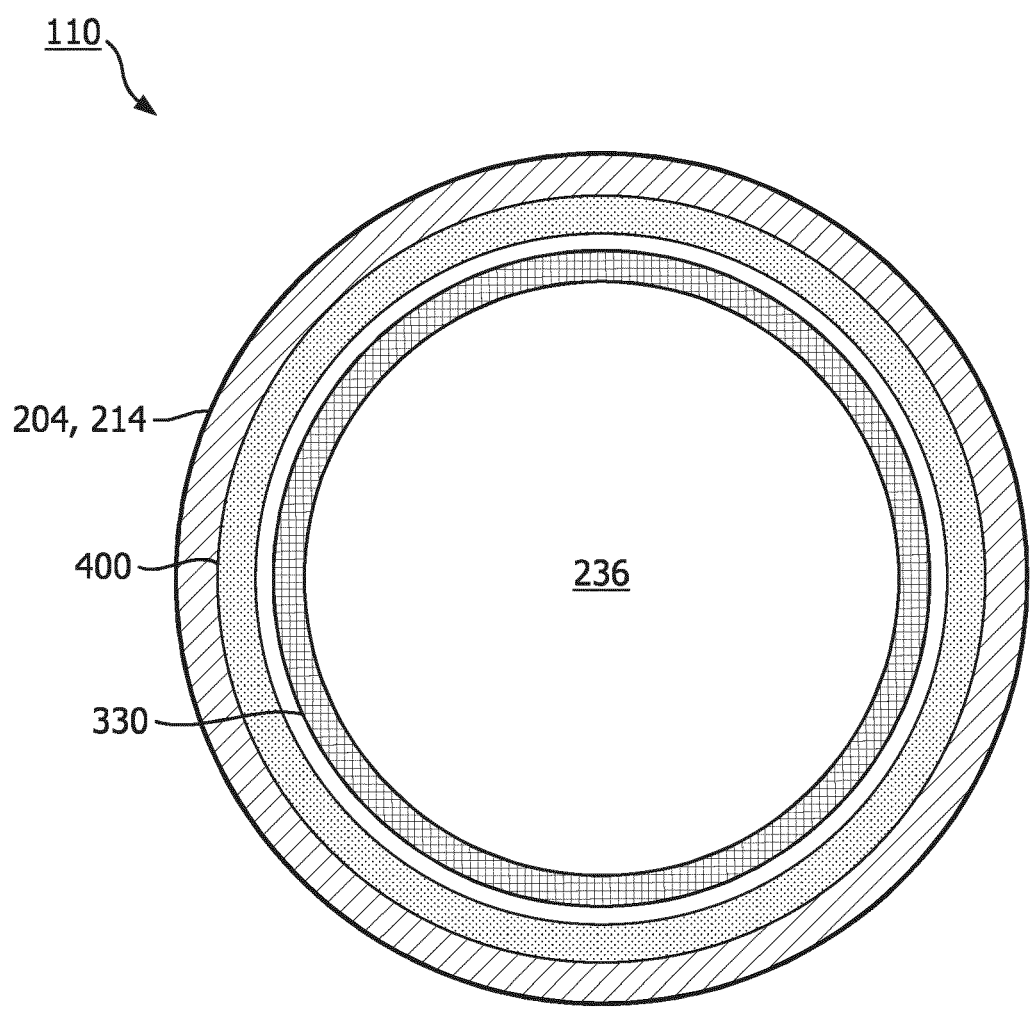
FIG. 13 is a diagrammatic end view of an imaging assembly along section lines 13-13 of FIG. 6.
Figure 14:
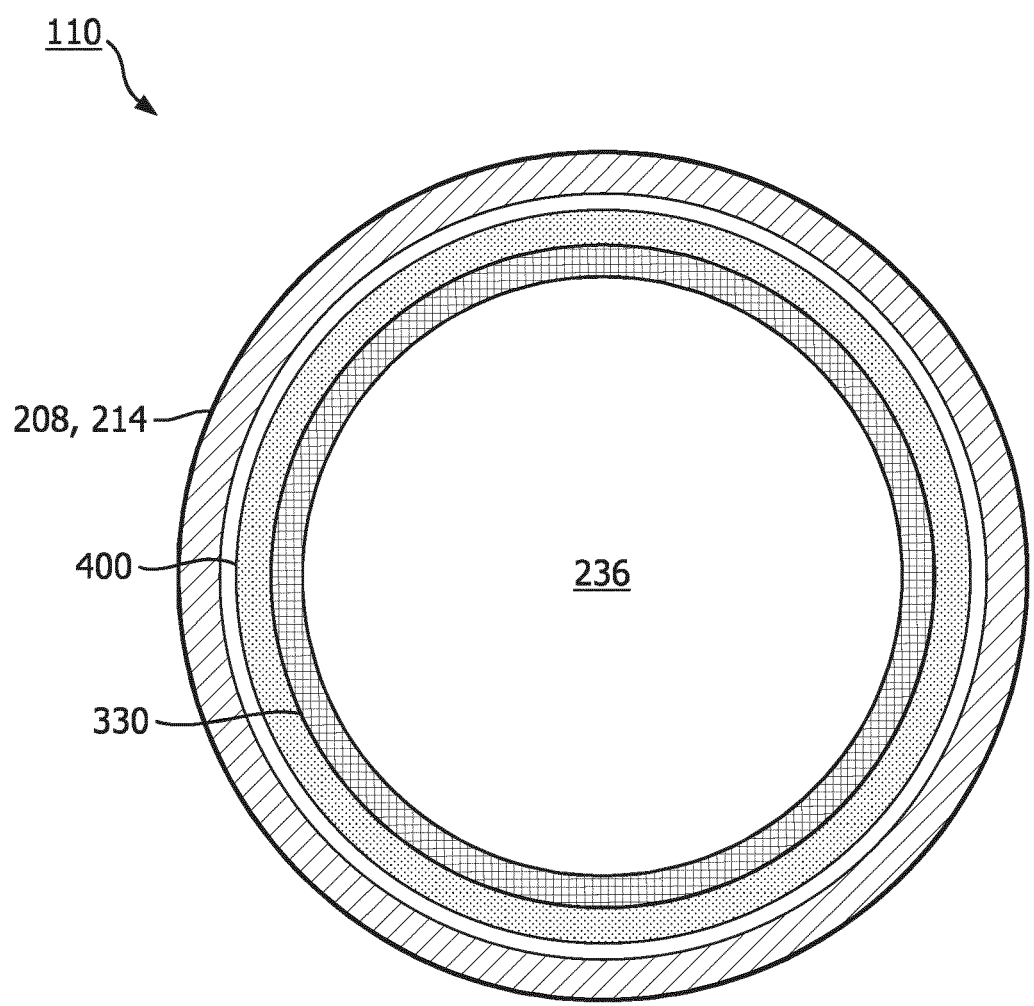
FIG. 14 is a diagrammatic end view of an imaging assembly along section lines 14-14 of FIG. 6.
Figure 15:
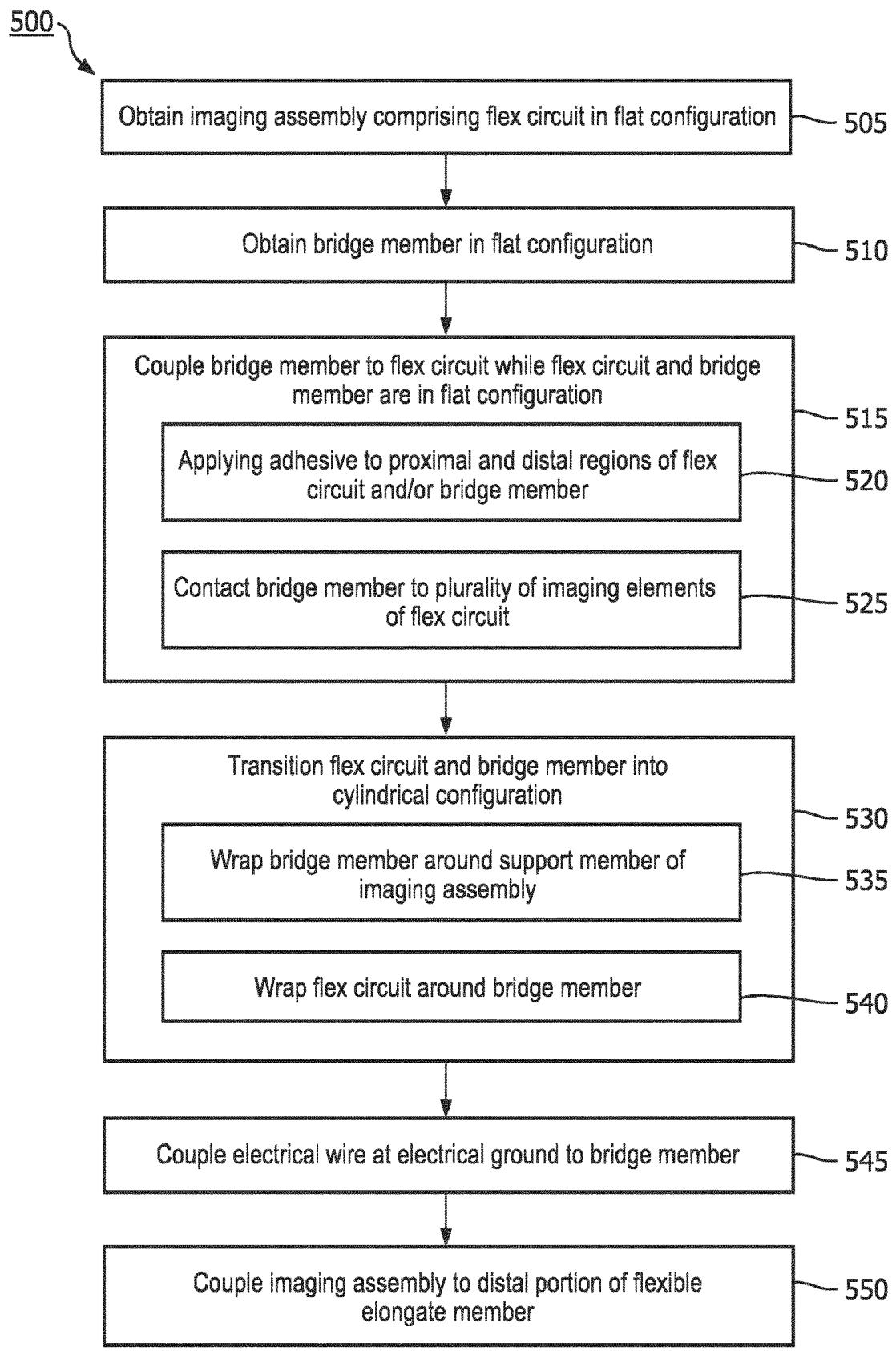
FIG. 15 is a flow diagram of a method of assembly an intraluminal imaging device, according to aspects of the present disclosure.

FIGS. 9, 10, 11, and 12 illustrate various stages in an exemplary method of assembling an intraluminal device, such as the intraluminal device 102. FIGS. 5, 6, 13, and 14 illustrate at least a portion of the assembled intraluminal device 102, such as the imaging assembly 110. FIG. 13 is cross-sectional end view along section lines 13-13 of FIG. 6. FIG. 14 is a cross-sectional end view along section lines 14-14 of FIG. 6. FIG. 15 is a flow diagram of a method 500 of assembling an intraluminal imaging device, as described herein. The method 500 will be described with reference to FIGS. 5, 6, 9, 10, 11, 12, 13, and 14. It is understood that the steps of method 500 may be performed in a different order than shown in FIG. 15, additional steps can be provided before, during, and after the steps, and/or some of the steps described can be replaced or eliminated in other embodiments. The steps of the method 500 can be carried out by a manufacturer of the intraluminal imaging device.

Figure 9:
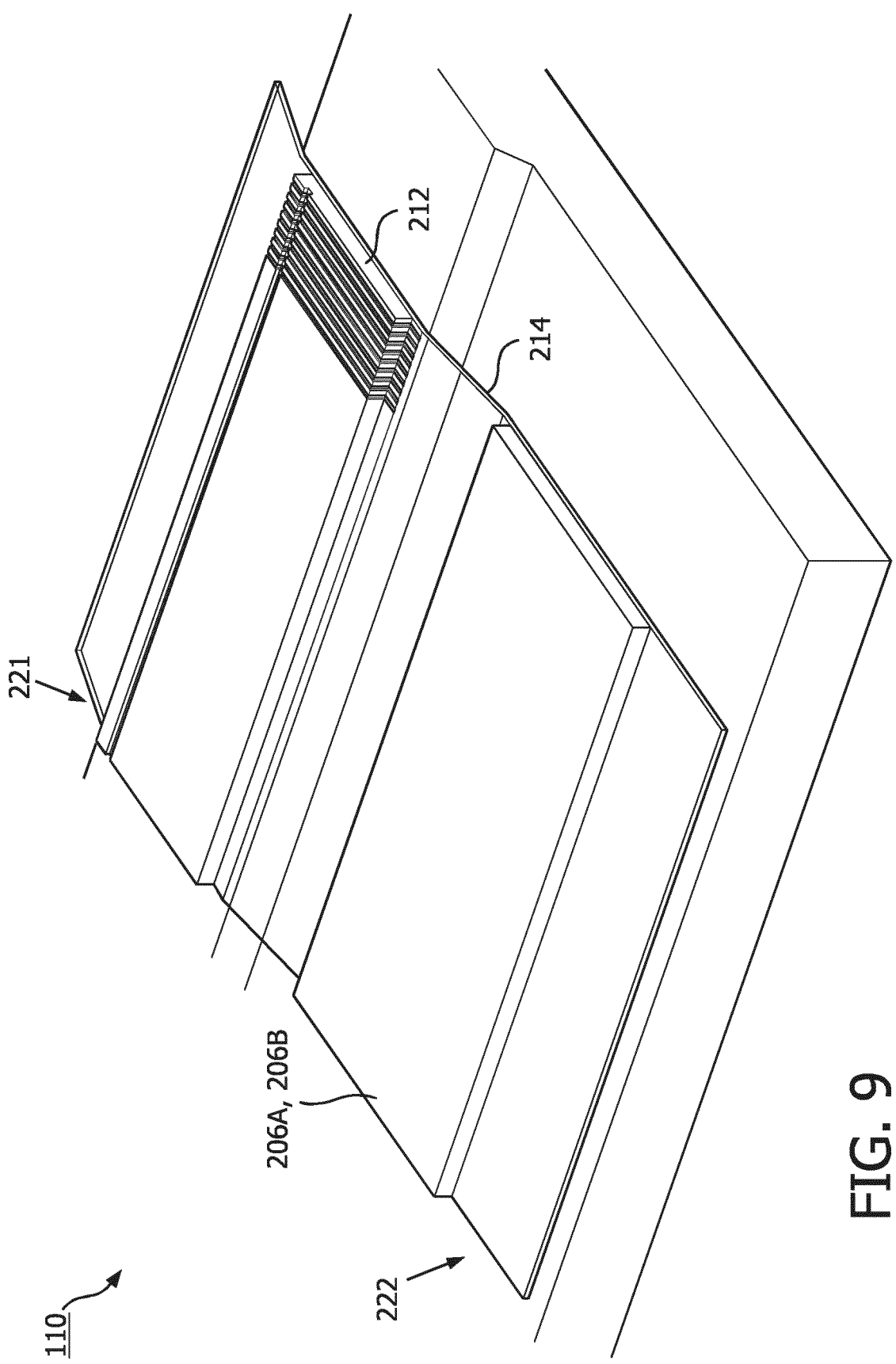
FIG. 9 is diagrammatic perspective view of a flex circuit in a flat configuration.

At step 505, the method 500 includes obtaining an imaging assembly comprising a flex circuit in a flat configuration. As shown in FIG. 9, for example, the imaging assembly 110 includes the flex circuit 214 arranged in a flat configuration. The flex circuit 214 includes the plurality of controllers 206A, 206B in communication with a plurality of transducers 212. Step 505 can include forming the imaging assembly 110. For example, the FIG. 9 may illustrate the transducer elements 212 while they are being singulated, such as by dicing. In that regard, the bridge member 400 can be coupled to the flex circuit during the same manufacturing process as the flex circuit 214 is formed. Generally, the imaging assembly 110, the flex circuit 214, the controllers 206A, 206B, and the transducers 212 may be formed according to any suitable process.

Figure 10:
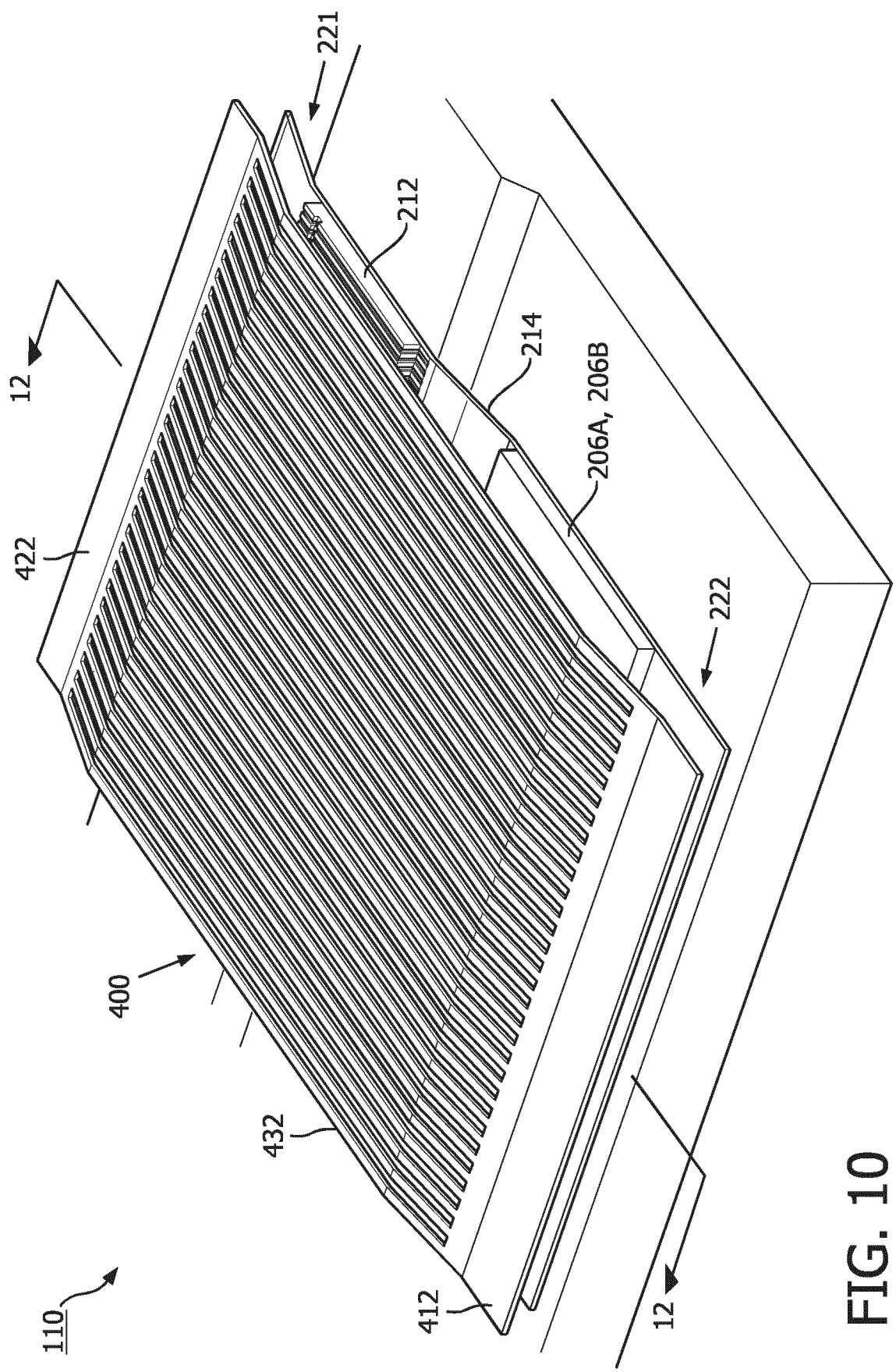
FIG. 10 is diagrammatic perspective view of a support member and a flex circuit in a flat configuration.

Referring again to FIG. 15, at step 510, the method 500 includes obtaining a bridge member in a flat configuration. In some embodiments, the method 500 can include forming the bridge member by any suitable process, including micromachining, 3D printing, wafer production processes, etc. As shown in FIGS. 10 and 11, the bridge member 400 is arranged in a flat configuration. In some embodiments, the method 500 includes bringing the bridge member 400 and/or the flex circuit 214 into proximity with one another such that the two are adjacent to one another.

Referring again to FIG. 15, at step 515, the method 500 includes couple the bridge member to the flex circuit while the flex circuit and the bridge member are in the flat configuration. As shown in FIGS. 10, 11, and 12, for example, the flex circuit 214 may be mechanically and/or electrically coupled to the bridge member 400. For example, the proximal portions 222 and 410 of the flex circuit 214 and the bridge member 400, respectively, can be coupled. The distal regions 221 and 420 of the flex circuit 214 and the bridge member 400, respectively, can be bonded. In some embodiments, step 515 includes applying adhesive to the proximal region 222 of the flex circuit 214, the distal region 221 of the flex circuit 214, the proximal region 410, and/or the distal region 420 of the bridge member 400 (step 520). In other embodiments, any suitable method of bonding can be used to mechanically couple the flex circuit 214 and the bridge member 400.

In some embodiments, step 515 can include contacting the bridge member 400 to a plurality of imaging elements of the flex circuit (step 525). As shown in FIG. 12, when the bridge member 400 is coupled to the flex circuit 214, the bridge member 400 contacts the transducer elements 212. In such embodiments, step 515 can include positioning the bridge member 400 and/or the flex circuit 214 such that the bridge member 400 contacts the transducer elements 212 without contacting the controllers 206A, 206B. In some embodiments, such as those in which the bridge member 400 is configured to provided electrical grounding for the controllers 206A, 206B, the bridge member 400 and/or the flex circuit 214 is positioned such that the bridge member 400 contacts the controllers 206A, 206B without contacting the transducer elements 212. In some embodiments, the bridge member 400 and/or the flex circuit 214 is positioned such that a portion of the bridge member 400 contacts the controllers 206A, 206B and a portion of the bridge member 400 contacts the transducer elements 212. In some embodiments, step 515 can include bonding the bridge member 400 to the flex circuit 214 such that the bridge member 400 remains in contact with the transducers 212 and/or the controllers 206A, 206B.

Referring again to FIG. 15, at step 530, the method 500 includes transitioning the flex circuit and the bridge member into a cylindrical or rolled configuration. Because the flex circuit and the bridge member are coupled (step 515), the flex circuit and the bridge member are moved into the cylindrical configuration simultaneously. In some embodiments, the method 500 additionally includes obtaining a support member. The support member may be formed of a non-conductive material. The support member can form part of the imaging assembly. In some embodiments, step 530 includes wrapping the bridge member around the support member in a cylindrical configuration (step 535). In some embodiments, step 530 includes wrapping the flex circuit around the bridge member in a cylindrical configuration (step 540). The cylindrical configuration of the flex circuit and the bridge member are illustrated in FIGS. 5, 6, 13, and 14. As shown in FIG. 13, for example, the bridge member 400 is in contact with the transducer region 204 of the flex circuit 214. As shown in FIG. 14, for example, the bridge member 400 is spaced from the controller region 208 of the flex circuit 214.

Referring again to FIG. 15, at step 545, the method 500 includes coupling an electrical wire to the bridge member. The electrical wires may be at electrical ground such that the bridge member, as well as one or more components of the flex circuit in contact with the bridge member, is also at electrical ground. Step 545 can include any suitable from of establishing electrical contact, including soldering, welding, etc.

At step 590, the method 500 includes coupling the imaging assembly to a distal portion of a flexible elongate member. The flex circuit can be positioned around the support member such that the inner diameter of the flex circuit contacts a backing material disposed between the support member and the flex circuit. The method 500 may include securing the flex circuit to the support member using one or more adhesives. The method 500 may also include curing the backing material, such as by using heat or light. The method 500 includes coupling the imaging assembly to one or more distal members and one or more proximal members to form the intraluminal device. In that regard, the distal member(s) and/or proximal member(s) can be coupled to the support member and/or the flex circuit. The one or more proximal members may be flexible elongate members (e.g., an inner member and/or an outer member) forming a length of the intraluminal device. The imaging assembly may be positioned at a distal portion of the intraluminal device. The distal member defines a distal-most end of the intraluminal imaging device. The method 500 can include introducing adhesive to affix the flex circuit and the support member and/or other components of the intraluminal imaging device.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging device, comprising:
    a flexible elongate member configured for insertion into a vessel of a patient, the flexible elongate member including a proximal portion and a distal portion;
    an imaging assembly positioned at the distal portion of the flexible elongate member, wherein the imaging assembly comprises:
        a flex circuit comprising a length between a proximal end and a distal end, wherein the flex circuit comprises a plurality of imaging elements, a plurality of controllers, and a plurality of conductive traces, wherein the plurality of controllers are in communication with the plurality of imaging elements via the plurality of conductive traces;
        a bridge member separate from the flex circuit and extending along the flex circuit for a majority of the length of the flex circuit;
        a support member defining a guidewire lumen such that the support member is directly adjacent to the guidewire lumen; and
        a backing material different than the support member,
    wherein the bridge member is positioned around the support member and the flex circuit is positioned around the bridge member,
    wherein the backing material is positioned between the flex circuit and at least one of the support member or the bridge member, such that the backing material is spaced from the guidewire lumen by the support member,
    wherein the bridge member comprises a proximal region comprising a first diameter, a central region comprising a second diameter smaller than the first diameter, and a distal region comprising a third diameter greater than the second diameter,
    wherein the bridge member is directly coupled to an electrical wire separate from the flex circuit,
    wherein the electrical wire is at electrical ground such that the bridge member is maintained at electrical ground via the electrical wire, and
    wherein the central region is in contact with at least a portion of the flex circuit such that the at least the portion of the flex circuit is maintained at electrical ground via the bridge member and the electrical wire and not via the support member.

2. The device of claim 1, wherein the support member comprises a non-conductive material and the bridge member comprises a conductive material.

3. The device of claim 1, wherein the bridge member is disposed in a cylindrical configuration around the support member.

4. The device of claim 1, wherein the flex circuit is disposed in a cylindrical configuration around the bridge member.

5. The device of claim 1, wherein the at least the portion of the flex circuit that is in contact with the central region comprises the plurality of imaging elements.

6. The device of claim 1,
    wherein the bridge member comprises a proximal end and a distal end,
    wherein the proximal end of the flex circuit and the proximal end of the bridge member are coupled, and
    wherein the distal end of the flex circuit and the distal end of the bridge member are coupled.

7. The device of claim 1, wherein the bridge member comprises a plurality of ribs.

8. The device of claim 7, wherein the central region comprises the plurality of ribs such that the plurality of ribs is in contact with the at least the portion of the flex circuit.

9. The device of claim 1,
    wherein the bridge member comprises a first transition region between the proximal region and the central region and a second transition region between the distal region and the central region,
    wherein the first and second transition regions include a larger diameter than the second diameter of the central region and a smaller diameter than the first and third diameters of the proximal and distal regions respectively.

10. The device of claim 1, wherein the bridge member is configured to be transitioned from a flat configuration into a cylindrical configuration.

11. The device of claim 1, wherein the electrical wire extends along a length of the flexible elongate member.

12. The device of claim 1, wherein the bridge member is disposed radially inward of the flex circuit along the majority of the length of the flex circuit.

13. The device of claim 1, wherein the bridge member is coupled to the flex circuit by an adhesive.

14. The device of claim 1, wherein the bridge member is radially spaced from the flex circuit along a portion of the length of the flex circuit.

15. The device of claim 1, wherein the support member comprises a flexible polymer.

16. The device of claim 1,
wherein the flex circuit comprises a first edge and an opposite second edge,
wherein when the flex circuit is positioned around the bridge member, the first edge and the second edge are adjacent.

17. A method of assembling an intraluminal imaging device, the method comprising:
obtaining a flex circuit in a flat configuration, the flex circuit comprising a length between a proximal end and a distal end, wherein the flex circuit comprises a plurality of imaging elements, a plurality of controllers, and a plurality of conductive traces, wherein the plurality of controllers are in communication with the plurality of imaging elements via the plurality of conductive traces;
obtaining a bridge member separate from the flex circuit and in a flat configuration;
obtaining a support member defining a guidewire lumen such that the support member is directly adjacent to the guidewire lumen;
obtaining a backing material different than the support member;
coupling the bridge member to the flex circuit while the flex circuit and the bridge member are in the flat configuration such that the bridge member extends along the flex circuit for a majority of the length of the flex circuit;
transitioning the flex circuit and the bridge member into a cylindrical configuration such that the bridge member is positioned around the support member and the flex circuit is positioned around the bridge member,
wherein the bridge member is directly coupled to an electrical wire separate from the flex circuit,
wherein the electrical wire is at electrical ground such that the bridge member is maintained at electrical ground via the electrical wire,
wherein the bridge member comprises a proximal region comprising a first diameter, a central region comprising a second diameter smaller than the first diameter, and a distal region comprising a third diameter greater than the second diameter, and
wherein the central region is in contact with at least a portion of the flex circuit such that the at least the portion of the flex circuit is maintained at electrical ground via the bridge member and the electrical wire and not via the support member; and
positioning the backing material between the flex circuit and at least one of the support member or the bridge member, such that the backing material is spaced from the guidewire lumen by the support member.

18. The method of claim 17,
wherein the support member is made of a non-conductive material, and
wherein the transitioning includes positioning the bridge member in a cylindrical configuration around the support member.

19. The method of claim 18, wherein the transitioning includes positioning the flex circuit in a cylindrical configuration around the bridge member.

20. The method of claim 17,
wherein the bridge member comprises a proximal end and a distal end,
wherein the coupling includes applying adhesive to at least one of the proximal end of the flex circuit, the distal end of the flex circuit, the proximal end of the bridge member, or the distal end of the bridge member.

21. The method of claim 17, wherein the coupling includes contacting the central region to the plurality of imaging elements such that the at least the portion of the flex circuit that is in contact with the central region comprises the plurality of imaging elements.

22. The method of claim 21, wherein the central region comprises a plurality of ribs such that the contacting includes contacting the plurality of ribs to the plurality of imaging elements.

* * * * *